United States Patent
Fischer et al.

[11] Patent Number: 5,987,348
[45] Date of Patent: Nov. 16, 1999

[54] ECG TRIGGERED MR IMAGING METHOD AND APPARATUS

[75] Inventors: Stefan E. Fischer; Samuel A. Wickline; Christine H. Lorenz, all of St. Louis, Mo.

[73] Assignees: Philips Electronics North America Corporation, New York, N.Y.; Barnes-Jewish Hospital, St. Louis, Mich.

[21] Appl. No.: 08/898,830

[22] Filed: Jul. 23, 1997

[51] Int. Cl.⁶ .................................................. A61B 5/055
[52] U.S. Cl. ............................................ 600/413; 600/512
[58] Field of Search .............................. 600/413, 512, 600/410, 411, 509, 517, 521

[56] References Cited

U.S. PATENT DOCUMENTS

| | | | |
|---|---|---|---|
| 4,136,690 | 1/1979 | Anderson et al. | 128/2.06 A |
| 4,850,370 | 7/1989 | Dower | 600/512 |
| 5,000,182 | 3/1991 | Hinks | 600/413 |
| 5,029,082 | 7/1991 | Shen et al. | 600/512 |
| 5,101,833 | 4/1992 | Schmid | 600/512 |
| 5,458,116 | 10/1995 | Egler | 600/512 |
| 5,477,144 | 12/1995 | Rogers et al. | 324/309 |
| 5,513,638 | 5/1996 | Usui | 600/413 |
| 5,526,813 | 6/1996 | Yoshida | 128/653.2 |
| 5,692,508 | 12/1997 | Simonetti et al. | 600/413 |
| 5,830,143 | 11/1998 | Mistretta et al. | 600/420 |

OTHER PUBLICATIONS

C. Lentner, Geigy Scientific Tables, Heart and Circulation, 45, 1990.

Ernest Frank, Ph.D., "An Accurate, Clinically Practical System for Spatial Vectrocardiography", Circulation vol. 13, May 1956, pp. 737–749.

Primary Examiner—Brian L. Casler
Attorney, Agent, or Firm—Dwight H. Renfrew

[57] ABSTRACT

A method of imaging a portion of a body placed in a static magnetic field by means of magnetic resonance (MR) includes the measurement of ECG data of the body in the form of a vector cardiogram, and determination of an acquisition period from the ECG data, including directional information in the vector cardiogram, in order to synchronize measurement of MR signals to a cyclic movement of the body.

22 Claims, 4 Drawing Sheets

ECG TRIGGERED MR IMAGING METHOD AND APPARATUS

BACKGROUND OF THE INVENTION

1. Field of the Invention

The invention relates to a method of imaging a portion of a body placed in a static magnetic field by means of magnetic resonance (MR), which method includes measurement of ECG data of the body, determining an acquisition period from the ECG data in order to synchronize measurement of MR signals to a cyclic movement of the body, generating an MR sequence during the acquisition period of RF fields and magnetic gradient fields, and reconstructing an image of the portion of the body from the MR signals. The invention further relates to an MR apparatus for carrying out such a method and to an ECG device suitable for use in an MR apparatus.

2. Description of Related Arts

Such a method and apparatus are known from U.S. Pat. No. 5,526,813.

As is well known a k-space is understood to be a spatial frequency domain in which an MR signal is measured along a trajectory and the measured values yield the inverse Fourier transformed values of the image of the body. The trajectory in the k-space is determined by the time integral of temporary gradient fields over a time interval from the excitation of the nuclear spins to the actual instant of measurement of the MR signal. Furthermore, gradients are understood as being temporary magnetic fields which are superposed on the steady magnetic field and cause a gradient of the static magnetic field in three respective orthogonal directions. Generally speaking in a 2-D imaging sequence, the gradient in a first direction is denoted as a read gradient, the gradient in a second direction as a phase-encoding gradient and the gradient in a third direction as a slice-encoding gradient.

In the known method the quality of MR images is improved by the synchronization of the acquisition of MR signals with a heart beat of the body. Hereto the acquisition period of the MR signals is determined from the measured ECG data, for example, from the R-wave. In order to reduce erroneous determination of the acquisition periods the ECG data is filtered. By the filtering, noise is reduced from the ECG data obtained from the body. An MR image of the region of the body is then reconstructed from a set of MR signals from the portion of the body measured during consecutive synchronized acquisition periods. A drawback of the known method is that the filtering of the ECG data may be unreliable and as a result erroneous acquisition periods may be determined from the filtered ECG data.

SUMMARY OF THE INVENTION

It is inter alia an object of the invention to reduce the determination of erroneous acquisition periods. To this end a method in accordance with the invention is characterized in that the measurement of ECG data comprises measurement of a vector cardiogram. In the context of the present Patent Application a vector cardiogram is to be understood as the registration of a time course of mean instantaneous spatial cardiac vectors during atrial and ventricular depolarization. Characteristic loops of the instantaneous vector which are formed in a measurement space are labeled as P, QRS and T trajectories or loops. The invention is based on the insight that the measured ECG data is not only disturbed by the RF pulses generated during the acquisition period but that the ECG data is also disturbed due to induction in the leads from electrodes on the body to an ECG device by switching of the gradients and induction of noise in the ECG signals itself induced by the blood flow in the presence of the static magnetic field. Furthermore, by measuring the vector cardiogram it is possible to incorporate directional information of the vector cardiogram in the determination of the acquisition period. The measured vector describes predetermined loops in certain planes, whereas the artifacts are dominant in different planes and directions. In this way it is possible to determine, for example, the R-wave of the heart beat. The acquisition period can then be triggered on, for example, the R-wave. Furthermore, the properties of the vector cardiogram can be applied to discriminate physiological parameters of the cardiogram from gradient switching noise. For example, a switched gradient applied on the static magnetic field induces a similar voltage difference in all leads. Thus the amplitude of the measured vector is altered by the changing gradient whereas the direction of the measured vector is not changed. This characteristic can be employed to discriminate, for example, the QRS complex from gradient switching noise. A further advantage of the method according to the invention is that during MR examination the diagnostic value of the ECG of the body can be further improved.

A particular version of the method in accordance with the invention is characterized in that the measurement of the vector cardiogram includes applying an arrangement of a plurality of electrodes at the body according to an orthogonal lead set. Orthogonal lead systems are known per see from C. Lentner, Geigy Scientific Tables, Heart and Circulation, 45, 1990. Orthogonal lead systems comprises leads perpendicular to each other and to the transverse, sagittal and vertical axes of the body, the amplitudes of the leads would be equal from a vectorial standpoint, and the leads would have the same strength and direction, not only for a single point, but for all points within the heart where electromotive forces are generated.

By employing the orthogonal lead set a simple model can be applied for the description of the polarization and depolarization of the heart. As a result the measured vector cardiogram can be decomposed in orthogonal vector components. Physiological parameters of the ECG, such as P wave, QRS complex and T wave, are forming characteristic loops in the projection planes. The projection of these three-dimensional loops on a plane spawned by two of the three orthogonal vector components can be parameterized. The obtained parameters can be compared with the parameters of a vector cardiogram of the body measured without the presence of the static magnetic field. Furthermore, artifacts of vector cardiogram measured within the static magnetic field caused by the interaction of blood flow and the static magnetic field are represented by loops described by different parameters in comparison with the parameters of the loops of the physiological parameters.

A further version of the method in accordance with the invention is characterized in that the arrangement of the plurality of electrodes comprises a corrected orthogonal lead set.

A further version of the method in accordance with the invention is characterized in the method comprises a further step of determination of a first actual value of a first discrimination function of the vector cardiogram, the acquisition period being determined from the first actual value and a first predetermined reference function. As a result of these steps the acquisition period can be obtained from, for example, the angle between an electrical axis of the heart and an instantaneous vector of the vector cardiogram. Another possibility is that the acquisition period is obtained from the scalar product of the instantaneous vector of the vector cardiogram and the electrical axis of the heart. The latter method provides a simple way to increase the ratio of the R-wave and the unwanted flow related artifact. It is also possible that the acquisition period is determined from a modulus of a normal vector of the plane described by three neighbor points of the vector cardiogram. This determination is based on the observation that during an R wave of the ECG a velocity of the instantaneous vector of the vector cardiogram is larger than a velocity of the instantaneous vector of the vector cardiogram during other periods of the ECG.

The reference function can be a fixed threshold based on a percentage of the maximum value of the first actual value, for example, a percentage of 75%. Another possibility is that instead of a threshold for the reference function, the reference function comprises a fuzzy logic. Fuzzy logic works with probabilities instead of a fixed threshold. I.e. if the instantaneous vector of the vector cardiogram is within a spherical region around the electrical axis of the heart, the probability that an R-wave is detected is high. This criterion can be combined with different other criteria, for example, local maximum detection: in a local maximum where the differences between neighbor points of the vector cardiogram are high, a large likelihood exists that these points represent an R-wave. Another criterion may be based on the observation that a possibility for a next R-wave is low shortly after detection of a first R-wave and increasing with advancing time. For example, after 80% of the standard time interval between two consecutive R-waves the probability for a next R wave becomes 1.

A further version of the method in accordance with the invention is characterized in that the method comprises a further step of obtaining a reference vector cardiogram and the determination of a reference value of the first discrimination function from the reference vector cardiogram, the acquisition period being determined from a combination of the first actual value, the reference value and a second predetermined reference function. As a result of these steps the actual value of the first discrimination function can be weighted with the reference value of the first discrimination function determined for the body placed outside the static magnetic field.

A further version of the method in accordance with the invention is characterized in that the method comprises a further step of determining a second actual value of a second discrimination function of the vector cardiogram, the acquisition period being determined from a combination of the first actual value, the second actual value and a second predetermined reference function. As a result the acquisition period can be determined by a weighted combination of the actual values of different discrimination functions, for example, the discrimination function of the scalar product of the instantaneous vector of the vector cardiogram and the electrical axis of the heart and the discrimination function of the angle between the instantaneous vector of the vector diagram and the electrical axis of the heart.

A further version of the method in accordance with the invention is characterized in that for determination of a direction of one electrode selected from the plurality of the electrodes with relation to an isocenter of the static magnetic field, the method comprises further steps of generation of a rotating magnetic field by periodically applying two orthogonal gradient fields, measurement of a direction signal induced in a coil comprising the selected electrode and the body by the rotating magnetic field, and determination of the direction of the selected electrode with relation to an isocenter of the static magnetic field from the measured direction signal. This is an easy way to determine the direction of the electrode with relation to the isocenter of the static magnetic field. The isocenter is the position within the static magnetic field in which the influence of the applied gradient field is substantially zero. The electrode position is important for adaptive filtering using gradient switching information and for calculation of a dipole vector model of the heart. A frequency of the rotating magnetic field can be chosen such that filtering and suppression of the ECG is easy. The phase of the measured signal can be used to determine the direction of the electrodes with respect to the isocenter. A further version of the method in accordance with the invention is characterized in that for determination of a position along a direction of a gradient field of an electrode selected from the plurality of electrodes, the method comprises further steps of generation of a first gradient field which amplitude depends linearly from the position along the direction of the gradient field and measurement of a first induced voltage in a coil comprising the selected electrode and the body, generation of a second gradient field which amplitude varies according to a quadratic or higher order function of the position along the direction of the gradient field and measurement of a second induced voltage in the coil, and determination of the position of the electrode along the direction of the gradient from a ratio of the first and second induced voltages.

The invention also relates to a method for obtaining ECG data of a body placed in a static magnetic field which body is subjected to an MR sequence comprising RF fields and magnetic gradient fields, characterized in that the method comprises the steps of measurement of a vector cardiogram of the body, determination of a first actual value of a first discrimination function of the vector cardiogram, and determination of the physiologic parameter from the first actual value and a first predetermined reference function. As a result a ECG of the body can be obtained for diagnostic purposes, virtually free from unwanted artifacts due to the generated RF fields, the applied gradients and the present static magnetic field.

An embodiment of an MR apparatus in accordance with the invention is characterized in that the means for the measurement of the ECG signals comprises means for measurement of a vector cardiogram.

An embodiment of an ECG device suitable for use in an MR apparatus in accordance with the invention is characterized in that the ECG device comprises means for measurement of a vector cardiogram of the body, and means for determination of a first actual value of a first discrimination function of the vector cardiogram.

These and other aspects of the invention will be apparent from and elucidated with reference to the embodiments described hereinafter.

DETAILED DESCRIPTION OF THE PREFERRED EMBODIMENTS

Figure 1:
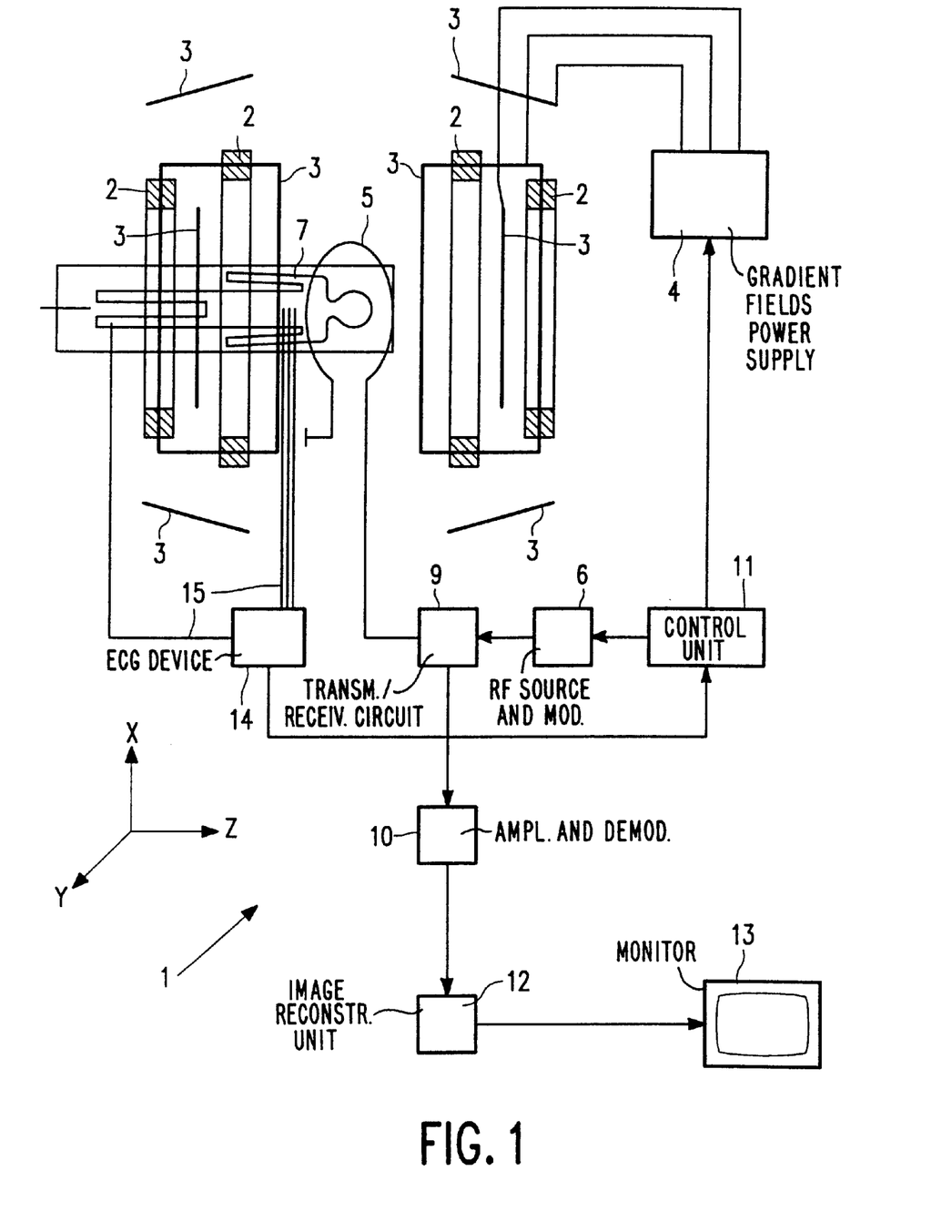
FIG. 1 shows an embodiment of an MR apparatus.

FIG. 1 shows an embodiment of an MR apparatus 1. The MR apparatus 1 comprises a first magnet system 2 for generating a steady magnetic field. The z-direction of the coordinate system shown corresponds to the direction of the steady magnetic field in the magnet system 2. The MR apparatus also comprises a second magnet system 3 for generating temporary magnetic fields directed in the z-direction and gradients in the x, y and z direction, respectively. It is to be noted that for ease of discussion x, y and z are used for the frequency encode, phase encode and slice selection direction, respectively. These directions do not have to coincide with the main directions of the system. Furthermore, in this Application the temporary gradient fields having a gradient in the x-direction, the y-direction and the z-direction are referred to as read gradient, phase-encode gradient and slice-selection gradient, respectively. Power supply means 4 feed the second magnet system 3. The magnet system 2 encloses an examination space which is large enough to accommodate a part of an object 7 to be examined, for example a part of a human body. An RF transmitter coil 5 serves to generate RF magnetic fields and is connected via a transmitter/receiver circuit 9 to an RF source and modulator 6. The RF transmitter coil 5 is arranged around the part of the body 7 in the examination space. The MR apparatus also comprises a receiver coil which is connected via the transmitter/receiver circuit 9 to a signal amplification and demodulation unit 10. The receiver coil and the RF transmitter coil 5 may be one and the same coil. A control unit 11 controls the modulator 6 and the power supply means 4 in order to generate MR imaging sequences comprising RF-pulses and temporary magnetic gradient fields. After excitation of nuclear spins in a part of the body placed within the examination space, the receiver coil 5 receives an MR signal. The phase and amplitude derived therefrom are sampled and further processed in the amplification and demodulation unit 10. An image reconstruction unit 12 processes the MR signals presented so as to form an image. The image is displayed, for example on a monitor 13. The control unit 11 also controls the image reconstruction unit 12. Furthermore, the MR device comprises an ECG device 14 to synchronize the generation of the MR image sequences with a cyclic movement of the body, for example, the heart beat of a body placed within the MR device. In order to measure an ECG signal the ECG device is connected in a known manner via electrodes 15 attached to the body. For example as described in Das Elektrokardiogram by R. Klinge, Thieme Verlag, 1987.

The ECG device generates a trigger signal for the control unit on the presence of, for example, the R-wave of the measured ECG. However, the presence of the static magnetic field generates artifacts in the ECG. The difference in the ECG measured with and without the presence of the static magnetic field is elucidated with reference to FIG. 2.

Figure 2:
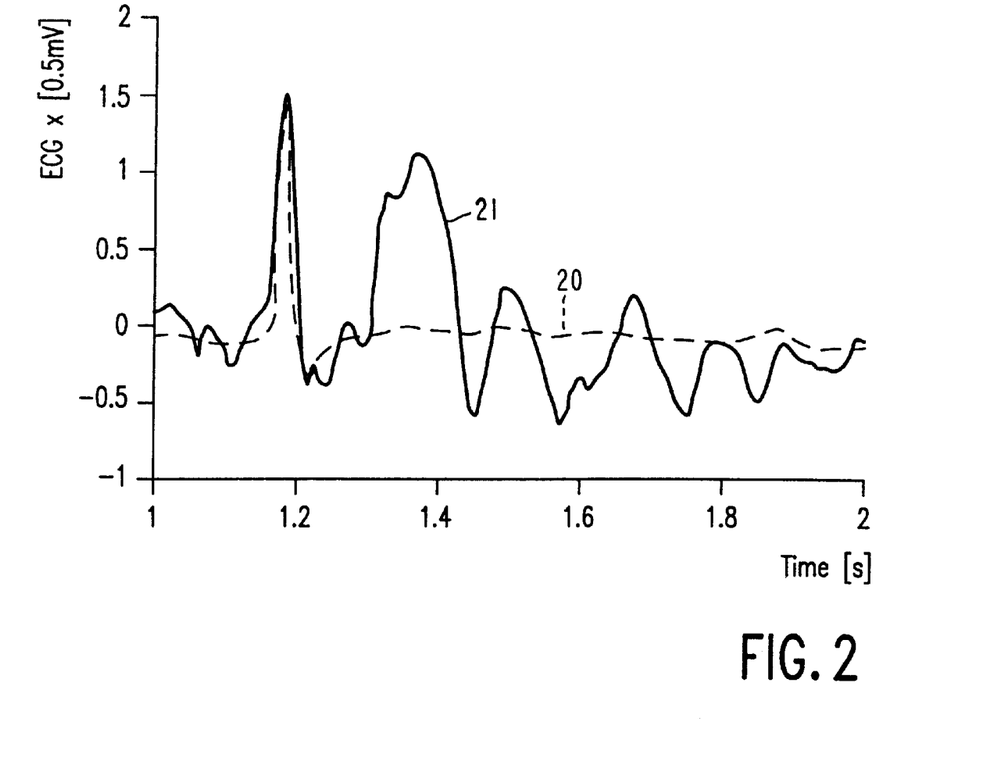
FIG. 2 shows two echo cardiograms measured according to a known method.

FIG. 2 shows a first and a second ECG of an healthy volunteer. The first ECG 20 is recorded without the presence of the static magnetic field of the MR device. The second ECG 21 is recorded in the presence of a static field of for example, 1.5 T of the MR device. The second ECG 21 recorded during the presence of the static magnetic field comprises several additional signals peaks compared to the first ECG 20. From the additional signal peaks erroneous acquisition periods can be determined.

In order to reduce the erroneous acquisition periods, in a method according to the invention the acquisition period is derived from a vector cardiogram obtained from the body instead of the ECG of the body. Thereto the ECG device measures a first reference vector cardiogram and an electrical axis of the heart before the body is placed in the MR apparatus. The vector cardiogram is measured after arranging a plurality of electrodes at the body according to a corrected orthogonal lead set. For example, a corrected orthogonal lead set comprising four electrodes. The signals of the four electrodes are converted to three signals $X_f$, $Y_f$, $Z_f$. The three signals $X_f$, $Y_f$, $Z_f$ describe the orthogonal lead system in which the leads are perpendicular to each other and to the transversal, sagittal and vertical axis of the body. Note that the orientation of the coordinate system $X_f$, $Y_f$, $Z_f$ is different from the coordinate system x,y,z of the MR device.

Figure 3:
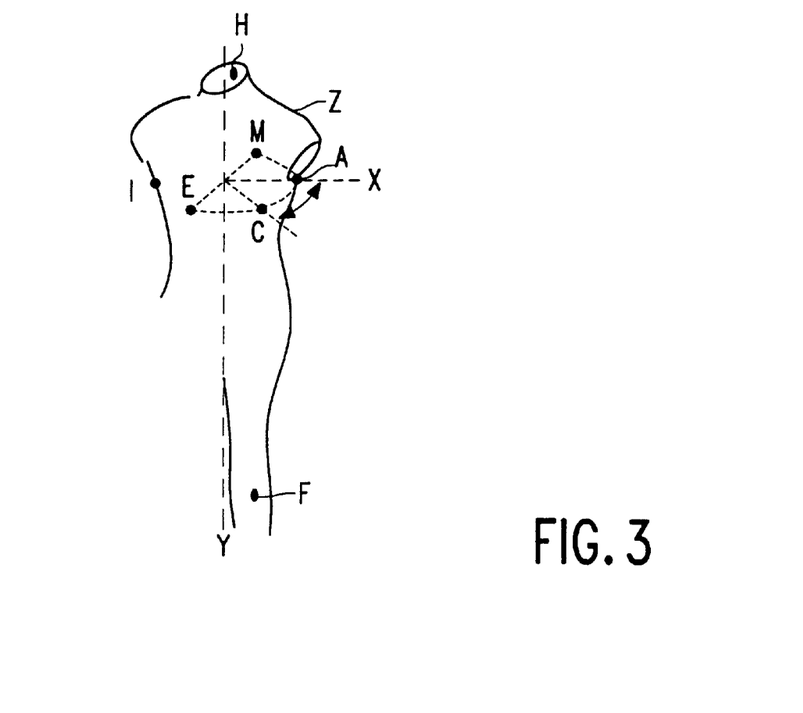
FIG. 3 shows the arrangement of electrodes of a Frank lead set is schematically drawn.

FIG. 3 shows an arrangement of the electrodes according to the Frank lead set. FIG. 3 shows seven electrode positions denoted as A,C,E,F,H,I and M A Frank lead set is known from an article by E. Frank as published in Circulation 13, page 737, 1956. Alternatively an electrode arrangement comprising 4 electrodes can be employed. Furthermore, the vector cardiogram is recorded in three standardized planes; i.e. frontal, transverse and left or right sagittal. These planes are defined by the orthogonal leads X, Y and Z. The XY-plane describes the frontal plane, the XZ-plane the transverse plane and ZY-plane the sagittal plane. In order to visualize the time course the vector loops can be interrupted for example each every 1 or 2 seconds.

Figure 4:
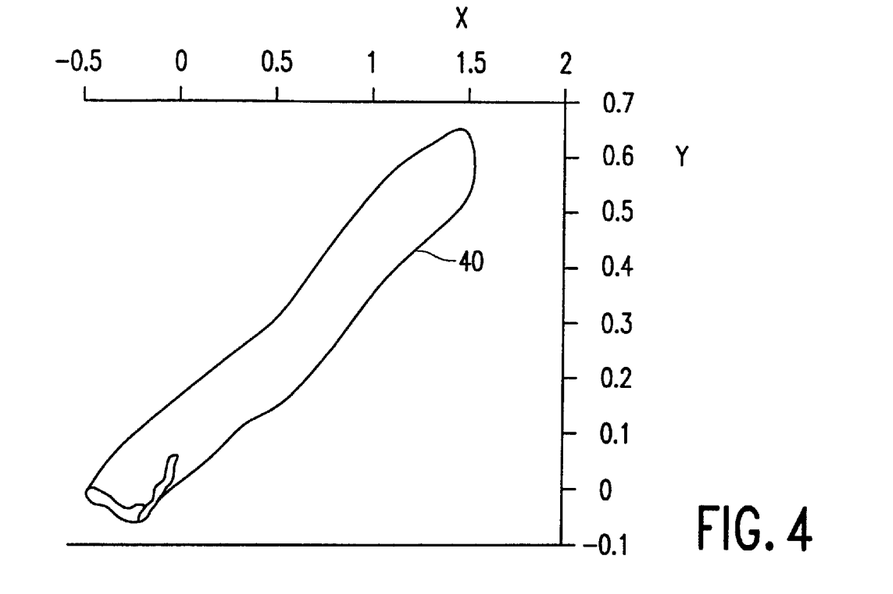
FIG. 4 shows a first vector cardiogram of a healthy volunteer without the presence of the static magnetic field.
Figure 5:
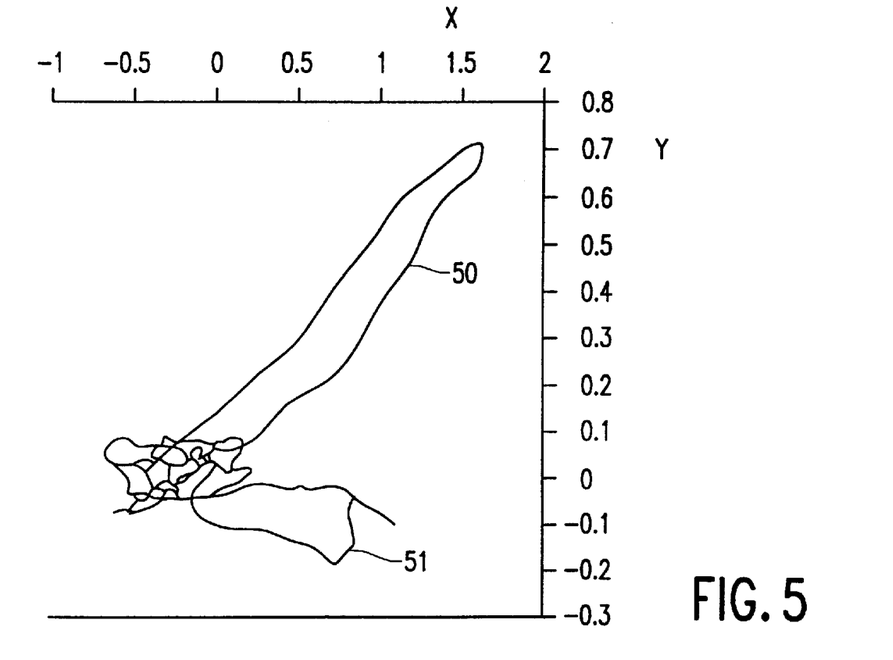
FIG. 5 shows a second vector cardiogram of a healthy volunteer in the presence of the static magnetic field.

Examples of vector cardiograms of a body with and without the presence of the static magnetic field to are shown in FIG. 4 and FIG. 5 to explain the methods according to the invention.

FIG. 4 shows a first projection 40 in the frontal or XY-plane of the QRS loop of a healthy volunteer without the presence of the static magnetic field. FIG. 5 shows a second projection 50 in the frontal plane of the QRS loop of the same healthy volunteer in the presence of a static magnetic field of, for example, 1.5 T parallel to the body axis. The second projection 50 of QRS loop is well preserved, whereas other loops, for example a loop 51 caused by interaction of blood flow and the static magnetic field can be observed in a different plane and direction than the plane and direction of the projection 50 of the QRS loop.

In order to reduce the number of erroneous acquisition periods in a method according to the invention a discrimination function is introduced that enlarges a difference between the QRS wave and the unwanted flow related artifact. The decision between the QRS wave and the unwanted flow related artifact is based on an actual value of the discrimination function and a predetermined reference function. In a first method of the invention a first discrimination function is defined, for example, as the scalar product of the instantaneous vector of the vector cardiogram and the electrical axis of the heart, in formula $$s_1(t) = |ECG(t)| \cdot |R| \cos \phi \qquad (1)$$

wherein φ represents the angle between the instantaneous vector and the vector R represents the electrical axis of the heart. In this way, for example, a ratio of 1 between the R-wave and the unwanted flow related artifact in the vector cardiogram can be improved to a ratio of 1.5. An example of a reference function is a fixed threshold of, for example, 75% of the maximum amplitude of the discrimination function $s_1(t)$.

In order to improve the differentiation of the R-wave and the blood flow related artifact the ration between the R-wave and the unwanted blood flow artefact can be increased by use of a scaled function $s_4$, defined as:

$$s_4(t) = \frac{s_1(t)}{|ECG(t) - R|^2},$$

wherein $s_1(t)$ represents the scalar product of the ECG and the vector R, R represents an R vector of the heart obtained outside the magnet. The signal $s_4(t)$ shows an increased R wave by a factor 3. A simple R-wave detection algorithm, for example, based on amplitude, a threshold of a value 4 and a first derivative can be applied on $s_4(t)$.

According to the invention said method can be implemented, for example, in the ECG device 14 of the MR apparatus 1. On basis of the actual value of the discrimination function of a measured vector cardiogram of the body and the fixed threshold the ECG device generates a trigger signal that is send to the control unit 11 in order to start an acquisition period.

Furthermore, in a second method of the invention a second discrimination function is defined, for example, as a weighting of the amplitude of the instantaneous vector of the vector cardiogram $V_{ecg}(t)$ and a function $f_w$, of the angle α between the instantaneous vector and the electrical axis of the heart in the following formula:

$$s_2(t) = V_{ecg}(t) \cdot f_w(\alpha) \quad (2)$$

An example of such a function $f_w$, is given by:

$$f_w = \frac{\pi - |\alpha(t) - \alpha(R)|}{\pi}.$$

A second reference function can be based again on a fixed threshold of, for example, 75% of the maximum values of the second discrimination function $s_2(t)$.

A third, more advanced, method according to the invention a third discrimination function is defined, for example, as the normal vector of a plane defined by three consecutive points of the vector cardiogram in the following formula:

$$v(t) = v_x, v_y, v_z = V_{ecg}(t) - V_{ecg}(t-dt) \times (V_{ecg}(t) - V_{ecg}(t+dt)) \quad (3)$$

wherein the defined normal vector can be regarded as the velocity v(t) of a vector cardiogram trajectory. A decision between the QRS wave and the unwanted flow artifact can then be based on the observation that during the R-wave the velocity v(t) of the vector cardiogram trajectory is larger then the velocity during the other periods. The duration of the R-wave lasts about 60 ms. A third reference function can be based for example on a fixed threshold of 90% of the maximum velocity of the vector cardiogram.

In a further method of the invention the modulus of v(t) can be weighted with the scalar product of velocity of the vector diagram trajectory obtained from a body in the presence of the static magnetic field and the velocity of a reference velocity of the vector cardiogram trajectory from the same body without the presence of the static magnetic field.

To reduce the number of erroneous acquisitions even more, in a fourth method of the invention a fourth discrimination function $s_3$ is defined based on a weighted combination of for example the decisions $D_1$, $D_2$, $D_3$ based on the first, second and third discrimination functions and their respective threshold values. For example $$s_3 = c_1 D_1(s_1) + c_2 D_2(s_2) + c_3 D_3(v(t)):$$

in which, for example $c_1 = c_2 = c_3 = 0.5$. A decision can be based on the value $s_3$ and a fixed threshold of 1.

Alternatively, in another method according to the invention a decision between the R-wave of the vector cardiogram and the unwanted flow related artifact is defined by fuzzy logic. The fuzzy logic is based on, for example, a combination of three possibility functions $P_1(t)$, $P_2(t)$, $P_3(t)$, wherein the first possibility function $P_1(t)$ is defined as a probability $P_1(t)$ that the end point of the instantaneous vector of the vector cardiogram being within a sphere of a radius d of the electrical axis R of the vector cardiogram in the following formula:

$$P_1(t) = \frac{1-d}{1+[|R-r|-d]}.$$

A second probability function $P_2(t)$ is defined as a local extremum, for example, a local maximum between two consecutive points of the vector cardiogram and the observation that the probability $P_2(t)$ is high during an R-wave in the following formula:

$$P_2(t) = \frac{1}{\max} \frac{r(t+\Delta t) - r(t)}{\Delta t}.$$

A third probability function $P_3(t)$ is a probability of the detection of a next subsequent R-wave after a recently detected R-wave and the observation that directly after a recently detected R-wave said probability $P_3(t)$ is low and after an elapsed interval t of 80 percent of the mean cycle time T of the heart said probability $P_3(t)$ is high. The following formula is used:

$$P_3(t) = \frac{0.2T + t}{T}$$

Another possibility to make a decision between the R-wave and an unwanted flow artifact can be based on, for example, a neural net that can be learned to recognize the predetermined patterns in the vector cardiogram.

Knowledge about the electrode location is important for adaptive filtering using gradient switching information and for calculation of the vector dipole model.

In order to determine the four electrode locations of the corrected orthogonal lead set arranged at the body in the MR apparatus according to the invention the control unit is further arranged to generate a special sequence comprising control signals, which are sent to the gradient amplifiers in order to apply a rotating magnetic gradient field on the static magnetic field. The method for determining the electrode location is explained with reference to FIG. 6.

Figure 6:
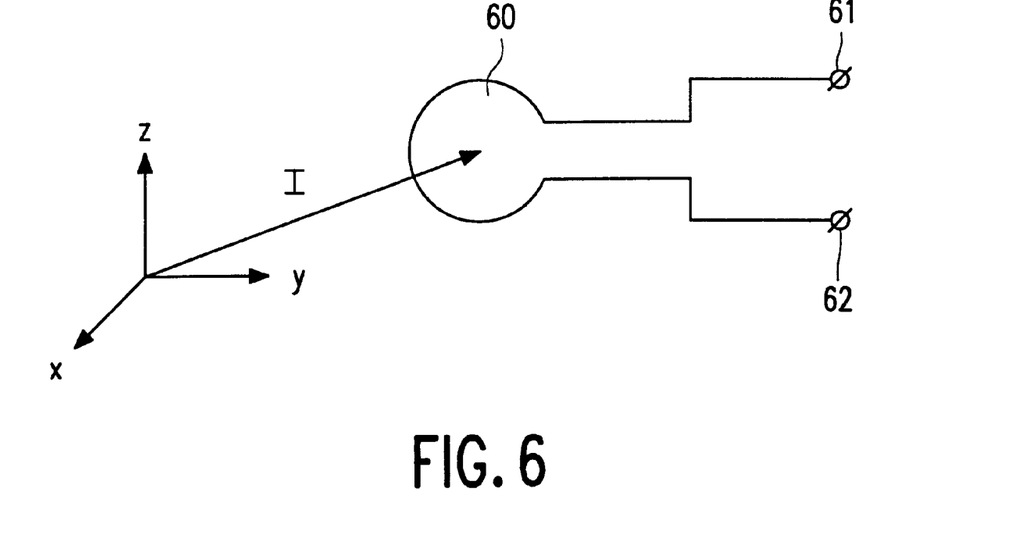
FIG. 6 shows a gradient coordinate system x,y,z and a position of a coil 60

FIG. 6 shows a gradient coordinate system x,y,z and a position of a coil 60. The coil 60 is formed by the leads, the body and the ECG device. The control unit generates the control signals to the gradient amplifiers such that the gradient system generates for example a rotating magnetic field in the x,y plane. The rotating magnetic field B(t) can be represented by:

$$B(t) = B_0 + r_x G \cos(\omega t) + r_y G \sin(\omega t),$$

wherein $B_0$ represents the static magnetic field, G represents the amplitude (in mT/m) of the gradient field and $\omega$ the frequency of the rotating magnetic field. The rotating magnetic gradient field induces a signal u(t) in the coil 60 given by the formula;

$$u(t) = S\frac{dB(t)}{dt} = GS \cos(\varpi t + \varphi),$$

wherein S represents the surface of the coil.

The induced signal can be measured on the connections 61,62 of the coil 60. Furthermore, the frequency $\omega$ of the rotating field is such that is the ECG information in the measured signal can be suppressed easily, for example, 100 Hz. The ECG information in the measured signal can be suppressed by, for example, a high pass filter that passes the electrode signal induced by the rotating gradient field. The phase $\phi$ of the filtered signal can be used to determine a direction of the measured electrode with respect to the isocenter of the gradients in the MR apparatus. This aspect of the invention is explained with reference to FIG. 7.

Figure 7:
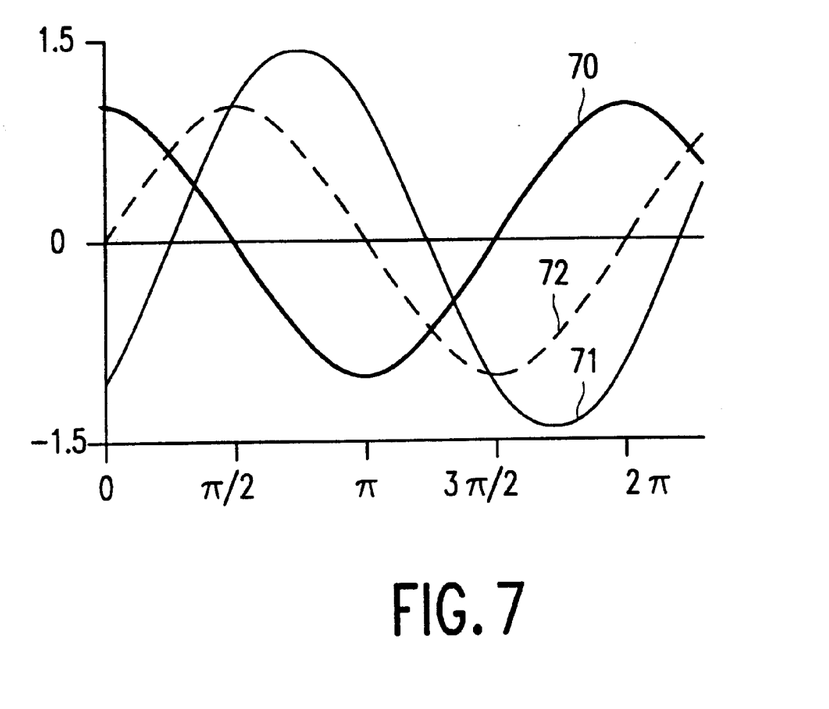
FIG. 7 shows the filtered electrode signal and a rotating gradient field as a function of time.

FIG. 7 shows a filtered electrode signal of an electrode at relative positions x=y=1. The uninterrupted thin line 72 represents the measured and filtered electrode signal, the interrupted line 71 represents the amplitude of the magnetic gradient field in the y-direction as a first sinusoidal function of time and the uninterrupted thick line 70 represents the amplitude of the magnetic gradient in the x-direction as a second sinusoidal function of time with a phase shift of $\pi/2$ with respect to the first sinusoidal function. The measured signal represents the induced voltage of both the gradients in the x- and y-directions, respectively. From the phase difference $\phi$ between for example the gradient in the x-direction and the induced voltage the direction of the location of the electrode with respect to the isocenter can be determined by the formula:

$$\varphi = \arctan\frac{r_x}{r_y},$$

Furthermore, the amplitude of the sinusoidal signal can be employed to determine a relative distance between the location of the electrode and the isocenter, since the amplitude of the filtered signal is proportional with the distance of the location of the electrode to the isocenter. Since the dimensions of the coil defined by the ECG leads and the body are not exactly known an absolute distance to the center of the coordinate system x,y,z cannot be determined from the received sinusoidal signal.

In order to determine an absolute position r ($r_x,r_y,r_z$) in the gradient coordinate system according to the invention x,y,z experiments has to be executed with linear and higher order gradients. In order to determine, for example, the distance r of a coil 60 in the coordinate system x,y,z as shown in FIG. 6 the gradient system generates a linear gradient field in the x-direction in a first experiment. During a rise time dt of the maximum gradient strength the voltage of the coil 60 is given as:

$$U_1 = S\frac{dG}{dt}r_x,$$

wherein $U_1$ represents the induced voltage on the connections 61,62, S represents the surface of the coil in the magnetic field G represent the amplitude of the gradient field and $r_x$ represents the component of the position along the x direction. Furthermore the gradient system generates a high order gradient, for example, a quadratic gradient field in a second experiment. During the rise time dt of the quadratic field the induced voltage $U_2$ in the coil 60 is given as:

$$U_2 = S\frac{dG}{dt}r_x^2.$$

The ratio of the voltage $U_1$ and the voltage $U_2$ yields the distance $r_x$ of the coil 60 in the gradient coordinate system. The distance $r_x$ is then given as $$r_x = \frac{U_2}{U_1}.$$

In order to determine the position ($r_x,r_y,r_z$) of the coil 60 in the gradient coordinate system x,y,z the described experiments has to be repeated in the y and z directions.

All references cited herein are incorporated herein by reference in their entirety and for all purposes to the same extent as if each individual publication or patent or patent application was specifically and individually indicated to be incorporated by reference in its entirety for all purposes.

We claim:

1. A method of imaging of a portion of a body placed in a static magnetic field by means of magnetic resonance (MR), which method comprises:
    measuring a vector cardiogram of the body,
    determining an acquisition period from the vector cardiogram in order to synchronize measurement of MR signals to a cyclic movement of the body, wherein the determining incorporates directional information from the measured vector cardiogram,
    generating an MR sequence during the acquisition period, the MR sequence comprising RF fields and magnetic gradient fields, and
    reconstructing an image of the portion of the body from the MR signals obtained during a plurality of cycles of the movement of the body.

2. A method as claimed in claim 1 wherein the measurement of the vector cardiogram includes applying an arrangement of a plurality of electrodes to the body according to an orthogonal lead set.

3. A method as claimed in claim 2 characterized in that the arrangement of the plurality of electrodes is in accordance with a corrected orthogonal lead set.

4. A method as claimed in claim 3, further comprising determining a first actual value of a first discrimination function of the vector cardiogram, the acquisition period being determined from the first actual value and a first predetermined reference function.

5. A method as claimed in claim 4, further comprising obtaining a reference vector cardiogram and determining a reference value of the first discrimination function from the reference vector cardiogram, the acquisition period being determined from a combination of the first actual value, the reference value and a second predetermined reference function.

6. A method as claimed in claim 5, wherein the acquisition period is determined from a combination of the first actual value, the second actual value, the reference value and a third predetermined reference function.

7. A method as claimed in claim 4, further comprising determining a second actual value of a second discrimination function of the vector cardiogram, the acquisition period being determined from a combination of the first actual value, the second actual value and a second predetermined reference function.

8. A method as claimed in claim 2, wherein for determining a direction of one electrode selected from the plurality of the electrodes with relation to an isocenter of the static magnetic field, the method further comprises generating a rotating magnetic field by periodically applying two orthogonal gradient fields, measuring a direction signal induced in a coil comprising the selected electrode and the body by the rotating magnetic field, and determining the direction of the selected electrode with relation to an isocenter of the static magnetic field from the measured direction signal.

9. A method as claimed in claim 2, wherein for determining a position along a direction of a gradient field of an electrode selected from the plurality of electrodes, the method further comprises generating a first gradient field which amplitude depends linearly from the position along the direction of the gradient field and measurement of a first induced voltage in a coil comprising the selected electrode and the body, generating a second gradient field which amplitude varies according to a quadratic or higher order function of the position along the direction of the gradient field and measuring a second induced voltage in the coil, determining the position of the electrode along the direction of the gradient from a ratio of the first and second induced voltages.

10. A method as claimed in claim 2, further comprising determining a first actual value of a first discrimination function of the vector cardiogram, the acquisition period being determined from the first actual value and a first predetermined reference function.

11. A method as claimed in claim 10, further comprising obtaining a reference vector cardiogram and determining a reference value of the first discrimination function from the reference vector cardiogram, the acquisition period being determined from a combination of the first actual value, the reference value and a second predetermined reference function.

12. A method as claimed in claim 11, wherein the acquisition period is determined from a combination of the first actual value, the second actual value, the reference value and a third predetermined reference function.

13. A method as claimed in claim 10, further comprising determining a second actual value of a second discrimination function of the vector cardiogram, the acquisition period being determined from a combination of the first actual value, the second actual value and a second predetermined reference function.

14. A method as claimed in claim 1, further comprising determining a first actual value of a first discrimination function of the vector cardiogram, the acquisition period being determined from the first actual value and a first predetermined reference function.

15. A method as claimed in claim 14, further comprising obtaining a reference vector cardiogram and determining a reference value of the first discrimination function from the reference vector cardiogram, the acquisition period being determined from a combination of the first actual value, the reference value and a second predetermined reference function.

16. A method as claimed in claim 15, wherein the acquisition period is determined from a combination of the first actual value, the second actual value, the reference value and a third predetermined reference function.

17. A method as claimed in claim 14, further comprising determining a second actual value of a second discrimination function of the vector cardiogram, the acquisition period being determined from a combination of the first actual value, the second actual value and a second predetermined reference function.

18. The method of claim 14, wherein the first discrimination function incorporates directional information from the measured vector cardiogram comprising an angle between an electrical axis of the heart generating the vector cardiogram and an instantaneous vector of the vector cardiogram, or a scalar product of the instantaneous vector of the vector cardiogram and the electrical axis of the heart, or a modulus of a normal vector to the plane defined by three neighboring points of the vector cardiogram.

19. The method of claim 17, wherein the second discrimination function incorporates directional information from the measured vector cardiogram comprising an angle between an electrical axis of the heart generating the vector cardiogram and an instantaneous vector of the vector cardiogram, or a scalar product of the instantaneous vector of the vector cardiogram and the electrical axis of the heart, or a modulus of a normal vector to the plane defined by three neighboring points of the vector cardiogram.

20. An MR device for the acquisition of images of a region of a body arranged in a substantially uniform steady magnetic field, the MR device comprising;

a) a magnet for generating the steady magnetic field, b) means for generating temporary magnetic gradient fields, c) means for generating RF pulses, d) means for measuring MR signals, e) means for measuring ECG signals, f) processing means for processing the MR signals measured so as to determine an image of the region of the body, h) a control unit synchronized by a trigger signal for the generation of control signals for the means for generating the gradients, and the means for the generating RF pulses, the control unit being arranged such that a plurality of sequences is generated, each sequence comprising RF fields and magnetic gradient fields and, i) synchronization means for determining the trigger signal for the control unit from the measured ECG signals in order to synchronize measurement of MR signals to a cyclic movement of the heart, wherein the means for the measurement of the ECG signals comprises means for measurement of a vector cardiogram, and wherein the synchronization means incorporates directional information from the measured vector cardiogram in order to synchronize measurement of the MR signals.

21. A method of determining a physiologic parameter of a body placed in a static magnetic field, which body is subjected to an MR sequence comprising RF fields and magnetic gradient fields, which the method comprises:

measuring a vector cardiogram of the body, determining a first actual value of a first discrimination function of the vector cardiogram, and wherein the first discrimination function incorporates directional information from the measured vector cardiogram, and determining the physiologic parameter from the first actual value and a first predetermined reference function.

22. An MR device as claimed in claim 21, wherein the ECG device comprises:

means for measurement of a vector cardiogram of the body, means for determination of a first actual value of a first discrimination function of the vector cardiogram, and generating means for generating of a trigger signal for the MR apparatus from the first actual value and a first predetermined reference function.

* * * * *